United States Patent [19]

Domb

[11] Patent Number: 5,188,837
[45] Date of Patent: Feb. 23, 1993

[54] LIPSOPHERES FOR CONTROLLED DELIVERY OF SUBSTANCES

[75] Inventor: Abraham J. Domb, Baltimore, Md.

[73] Assignee: Nova Pharmaceutical Corporation, Baltimore, Md.

[21] Appl. No.: 770,706

[22] Filed: Oct. 3, 1991

Related U.S. Application Data

[63] Continuation of Ser. No. 435,546, Nov. 13, 1989, abandoned.

[51] Int. Cl.$^5$ .................... A61K 31/47; A01N 25/00
[52] U.S. Cl. .................... 424/450; 424/405; 424/417; 264/46; 428/402.2
[58] Field of Search .................... 424/450, 1.1, 9, 403, 424/405, 417; 514/937, 938, 939, 943; 264/4.1–4.6; 436/829; 428/402.2

[56] References Cited

U.S. PATENT DOCUMENTS

| | | | |
|---|---|---|---|
| 3,004,892 | 10/1981 | Hainsworth et al. | 167/66 |
| 3,159,545 | 12/1964 | Kidwell et al. | 167/83 |
| 3,159,600 | 12/1964 | Watkins | 260/46.5 |
| 3,804,776 | 4/1974 | Yazawa et al. | 252/316 |
| 3,957,971 | 5/1976 | Oleniacz | 424/70 |
| 3,993,754 | 11/1976 | Rahman et al. | 424/177 |
| 4,004,548 | 2/1989 | Sharma et al. | 426/96 |
| 4,010,038 | 3/1977 | Iwasaki et al. | 106/22 |
| 4,025,455 | 5/1977 | Shackle | 252/316 |
| 4,029,762 | 6/1977 | Galanos et al. | 424/87 |
| 4,089,801 | 5/1978 | Schneider | 252/316 |
| 4,145,410 | 3/1979 | Sears | 424/19 |
| 4,168,308 | 9/1979 | Wretlind et al. | 424/244 |
| 4,186,183 | 1/1980 | Steck et al. | 424/38 |
| 4,201,767 | 5/1980 | Fullerton et al. | 424/89 |
| 4,224,179 | 9/1980 | Schneider | 252/316 |
| 4,235,871 | 11/1980 | Papahadjopoulos et al. | 424/19 |
| 4,280,996 | 7/1981 | Okamoto et al. | 424/199 |
| 4,298,594 | 11/1981 | Sears et al. | 424/19 |
| 4,310,506 | 1/1982 | Baldeschwieler et al. | 424/1 |
| 4,317,743 | 3/1982 | Chang | 252/316 |
| 4,331,654 | 5/1982 | Morris | 424/38 |
| 4,332,796 | 6/1982 | Los | 424/229 |
| 4,349,529 | 9/1982 | Morcos et al. | 424/1 |
| 4,356,167 | 10/1982 | Kelly | 424/38 |
| 4,377,567 | 3/1983 | Geho | 424/1 |
| 4,404,183 | 9/1983 | Kawata et al. | 424/19 |
| 4,434,153 | 2/1984 | Urquhart et al. | 424/22 |
| 4,438,052 | 3/1984 | Weder et al. | 264/4.6 |
| 4,439,194 | 3/1984 | Harwood et al. | 604/890 |
| 4,446,165 | 5/1984 | Roberts | 426/602 |
| 4,448,765 | 5/1984 | Ash et al. | 424/14 |
| 4,460,560 | 7/1984 | Tokes et al. | 424/1.1 |
| 4,485,054 | 11/1984 | Mezei et al. | 264/4.6 |
| 4,492,720 | 1/1985 | Mosier | 427/213.3 |
| 4,515,736 | 5/1985 | Deamer | 264/4.3 |
| 4,544,545 | 10/1985 | Ryan et al. | 424/1.1 |
| 4,563,354 | 1/1986 | Chang et al. | 424/195.1 |
| 4,610,868 | 9/1986 | Fountain et al. | 424/9 X |
| 4,622,219 | 11/1986 | Haynes | 424/450 |
| 4,725,442 | 2/1988 | Haynes | 424/490 |
| 4,752,485 | 6/1988 | Sharma et al. | 426/99 |
| 4,761,288 | 8/1988 | Mezel | 424/450 |
| 4,794,000 | 12/1988 | Ecanow | 424/457 |
| 4,797,288 | 1/1989 | Sharma et al. | 424/476 |
| 4,816,247 | 3/1989 | Desai et al. | 514/943 |
| 4,828,857 | 5/1989 | Sharma et al. | 426/285 |
| 4,880,634 | 11/1989 | Speiser | 424/450 |
| 4,894,233 | 1/1990 | Sharma et al. | 424/440 |
| 4,894,234 | 1/1990 | Sharma et al. | 424/440 |
| 4,911,928 | 3/1990 | Wallach | 424/450 |
| 4,914,084 | 4/1990 | Ecanow | 514/6 |
| 4,929,508 | 5/1990 | Sharma et al. | 424/439 |
| 4,933,183 | 6/1990 | Sharma et al. | 424/439 |
| 4,935,242 | 6/1990 | Sharma et al. | 424/439 |
| 4,963,363 | 10/1990 | Forssen | 424/450 |
| 4,963,367 | 10/1990 | Ecanow | 424/485 |
| 4,973,465 | 11/1990 | Baurain et al. | 424/406 |

FOREIGN PATENT DOCUMENTS

| | | |
|---|---|---|
| 0042249 | 12/1981 | European Pat. Off. |
| 0167825 | 1/1986 | European Pat. Off. |
| 0177368 | 4/1986 | European Pat. Off. |
| 0270460 | 6/1986 | European Pat. Off. |
| 0209870 | 1/1987 | European Pat. Off. |
| 0274431 | 7/1988 | European Pat. Off. |
| 2601207A1 | 7/1976 | Fed. Rep. of Germany |
| WO83/00294 | 2/1983 | PCT Int'l Appl. |
| WO8500011 | 1/1985 | PCT Int'l Appl. |
| 2135647A | 5/1984 | United Kingdom |

OTHER PUBLICATIONS

Friedman, et al., *Drug Development and Industrial Pharmacy* 13(9–11), 2067 (1987).
Gasco, et al., *Il Farmaco—Ed. Pr.* 43(10), 326 (1987).
Gasco, et al., *International Journal of Cosmetic Science* 10(6), 263 (1988).
Kawamata, et al., *Journa of Pharmaceutical Sciences* 76(11), S275, Abstract No. N 04-W-19 (1987).
Schmidt, et al., *Acata Pharmaceutica Technologica* 38(1), 34 (1989).
Wang, et al., *Journal of Pharmaceutical Sicences* 76(11), S305, Abstract No. N 07-W-21 (1987).
Wang, et al., *Journal of Pharmaceutical Sciences* 76(11), S205, Abstract No. N 07-W-22 (1987).
Sasaki, et al, *J. Pharm. Dyn.* 7, 120–130 (1984).
Venkatesh, et al., *Journal of Pharmaeutical Sciences* 76(11), S305, Abstract No. N 07-W-19 (1987).
Gao and Huang, *Biochim. Biophys. Acta* 897, 377–383 (1987).

Primary Examiner—Thurman K. Page
Assistant Examiner—G. S. Kishore
Attorney, Agent, or Firm—Kilpatrick & Cody

[57] ABSTRACT

A microsuspension system and method for its preparation is disclosed. The microsuspension contain lipospheres, which are solid, water-insoluble microparticles that have a layer of a phospholipid embedded on their surface. The core of the liposphere is a solid substance to be delivered, or a substance to be delivered that is dispersed in an inert solid vehicle, such as a wax.

21 Claims, No Drawings

LIPOSPHERES FOR CONTROLLED DELIVERY OF SUBSTANCES this is a continuation of copending application Ser. No. 07/435,546 filed on Nov. 13, 1989, now abandoned.

BACKGROUND OF THE INVENTION

This invention is in the area of controlled delivery systems for substances, including pharmaceuticals.

Many dispersion systems are currently in use as, or being explored for use as, carriers of substances, particularly biologically active compounds. These systems are designed to protect the substance from the environment during delivery and to provide a controlled release of the substance to a targeted area. In some cases, the goal is to target specific sites in the body using the dispersion. In other cases, the goal is to prepare a drug carrier system that acts as a reservoir at the site of injection. Dispersed systems for delivery are also important in the non-pharmaceutical area, for example, for use in the controlled release of substances such as insecticides, fungicides, herbicides and pheromones.

Dispersion systems used for pharmaceutical and cosmetic formulations can be categorized as either suspensions or emulsions. Suspensions are defined as solid particles ranging in size from a few nanometers up to hundreds of microns, dispersed in an aqueous or nonaqueous medium using suspending agents. Solid particles include microspheres, microcapsules, and nanospheres.

Emulsions can be defined as dispersions of one liquid in another, stabilized by an interfacial film of emulsifiers such as surfactants and lipids. Despite their long history, emulsions are used less often today than many other dosage forms due to the inherent instability. Emulsion formulations include water in oil and oil in water emulsions, multiple water/oil/water emulsions, microemulsions, microdroplets, and liposomes.

Microdroplets are unilamellar phospholipid vesicles that consist of a spherical lipid layer with an oil phase inside, as defined in Haynes U.S. Pat. No(s). 4,622,219 and 4,725,442. These phospholipid coated microdroplets of hydrophobic liquid drugs, or drugs dissolved in an organic solvent, can be used as a means to deliver a water insoluble general anesthetic to a local region of the body.

Liposomes are phospholipid vesicles prepared by mixing water-insoluble polar lipids with excess water or an aqueous solution. The unfavorable entropy caused by mixing the insoluble lipid in the water produces a highly ordered assembly of concentric closed membranes of phospholipid with entrapped aqueous solution. The membrane consists of a bimolecular sheet of lipid molecules that have their hydrophobic centers aligned in the middle of the membrane, and hydrophilic ends on the outside of the membrane, interfacing with the aqueous solution, and on the inside, interfacing with entrapped aqueous solution. A unilamellar liposome has a single membrane encapsulating a solution. A multilamellar liposome has a series of membranes, each of which is separated from the neighboring membrane by water. Unilamellar liposomes have a minimum size of about 25 nanometers in diameter, while multilamellar liposomes can range up to several micrometers. The rigidity and permeability of phospholipid bilayers can be adjusted by including other water-insoluble components such as sterols and amphiphiles with the phospholipid.

As noted above, while emulsion based delivery systems are useful for certain applications, the delivering vesicles are subject to physical rupture because of the delicate nature of the liquid/membrane/liquid structure. Emulsion based delivery systems also have relatively short release times. Further, it is difficult to isolate emulsion based vesicles from the aqueous media used for storage for subsequent reconstitution.

The solid phase vesicles in suspension based delivery systems are more stable than the liquid vesicles in emulsion based delivery systems. However, in suspension based systems the concentration of the suspension and the interaction between the vesicles and the liquid carrier is limited because of the repulsive interaction between the solid and the carrier.

It is therefore an object of the present invention to provide a controlled delivery system for substances that is stable for an extended time.

It is another object of the present invention to provide a controlled delivery device that has a relatively long release time.

It is still another object of this invention to provide a suspension delivery vesicle that can be isolated for storage and then resuspended when desired.

SUMMARY OF THE INVENTION

A microsuspension system and method for its preparation is disclosed. The microsuspension contains lipospheres, which are solid, water-insoluble microparticles that have a layer of a phospholipid embedded on their surface. The core of the liposphere is a solid substance to be delivered, or a substance to be delivered that is dispersed in an inert solid vehicle, such as a wax.

Lipospheres can be prepared by: (1) melting the substance to be delivered, or dissolving or dispersing the substance to be delivered in a molten vehicle to form a liquid of the substance to be delivered which can be solidified without changing vehicles; (2) adding the phospholipid along with an aqueous medium to the melted substance or vehicle at a temperature higher than the melting temperature of the substance or vehicle to form a suspension; (3) mixing the suspension at a temperature above the melting temperature of the vehicle until a homogeneous fine preparation is obtained; and then (4) rapidly cooling the suspension to room temperature or below the melting point of the liquified vehicle.

When dispersed in an aqueous solution, the product is a uniform fine dispersion of solid microparticles coated with a layer of a phospholipid, wherein the hydrophobic side of the phospholipid is embedded in the surface of the solid hydrophobic core and the hydrophilic side of the phospholipid interfaces with the aqueous solution.

DETAILED DESCRIPTION OF THE INVENTION

The claimed invention is a new type of microsuspension and a method for its preparation. The microsuspension is formulated by suspending in an aqueous solution solid, water-insoluble microparticles, called lipospheres, that have a phospholipid layer embedded on their surface. The solid portion of the lipospheres can be either a solid substance to be delivered, or a substance dispersed in an inert solid vehicle, such as a wax.

The lipospheres prepared as described herein are distinct from microdroplets or liposomes since the lipospheres have solid inner cores at room temperature and the phospholipid coating is entrapped and fixed to the particle surface. The lipospheres are distinct from microspheres of uniformly dispersed material or homogenous polymer since they consist of at least two layers, the inner solid particle and the outer layer of phospholipid.

The combination of solid inner core with phospholipid exterior confers several advantages to the liposheres over microspheres and microparticles, including being highly dispersible in an aqueous medium, and having a release rate for the entrapped substance which is controlled by the phospholipid coating. There are also many advantages over other dispersion based delivery systems. Liposheres have increased stability as compared to emulsion based delivery systems and are more effectively dispersed than most suspension based systems. Further, the substance to be delivered does not have to be soluble in the vehicle since it can be dispersed in the solid carrier. Further, in a liposphere, there is no equilibrium of substance in and out of the vehicle as in an emulsion system. Liposheres also have a lower risk of reaction of substance to be delivered with vehicle than in emulsion systems because the vehicle is a solid inert material. Moreover, the release rate of the substance from the liposheres can be manipulated by altering either or both the inner solid vehicle or the outer phospholipid layer.

Pharmaceutical uses of the liposheres include in extended release injectable formulations; in oral formulations for release into the lower portions of the gastrointestinal tract; in oral formulations to mask the taste or odor of the substance to be delivered; and as components in lotions and sprays for topical use, for example, in dermal, inhalation, and cosmetic preparations.

Non-pharmaceutical uses for liposheres include delivery of food additives, including stabilizers and dispersants or other viscosity modifying agents, controlled and selective delivery of pesticides, herbicides, insecticides, and pheromones, and in color and ink formulations in the printing and ink industry.

The preparation and modification of liposheres is described first with reference to the following general descriptions and then with reference to the following non-limiting examples of the preparation and application of liposheres.

I. Selection of the Solid Core of the Liposphere

The liposphere contains a core that has a melting temperature of 30° C. or higher. This can be accomplished by choosing a substance to be delivered that has a melting temperature above 30° C., or by mixing the substance to be delivered in a carrier or vehicle to produce a mixture having a melting point above 30° C.

The melting point of the substance to be delivered, alone or in combination with the carrier, should preferably be below 120° C. The substance, or substance and carrier, should also be stable in the liquid form when mixed with hot aqueous media.

The carrier for medical applications must be compatible with the substance to be delivered. Suitable pharmaceutical solid carriers are inert hydrophobic biocompatible materials with a melting range between 30° and 120° C. Examples are natural, regenerated or synthetic waxes such as beeswax and carnauba wax; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard and soft paraffins; hard fat such as tristearin; biodegradable polymers such as polycaprolactone, polyamides, polyanhydrides, polycarbonates, polyorthoesters, polylactic acids, and copolymers of lactic acid and glycolic acid; cellulose derivatives and mixtures thereof. These materials are known to those skilled in the art and commercially available, as demonstrated by the extensive list of suitable carrier materials in Martindate, *The Extra Pharmacopoeia*, The Pharmaceutical Press, 28th Edition pp 1063–1072 (1982).

For nonmedical applications, the vehicle can be a degradable or nondegradable material that melts at temperatures of 30° C. to 120° C. Such as: polyamides, polyolephines, polyesters, and cellulose derivatives.

Examples of biologically active compounds for delivery by liposheres are water insoluble drugs such as nonsteroidal anti-inflammatory compounds, local anesthetics, water insoluble chemotherapeutic agents, and steroids.

The release rate of the substance from the liposphere is dependent in part upon the composition of the core, as well as the outer phospholipid layer, and can be altered by varying the composition appropriately.

It is often desirable to deliver a water soluble substance to a targeted area, or to control the release of a water soluble substance. Since the inner core of the liposphere is hydrophobic, it is necessary to decrease the water solubility of such compounds before liposphere preparation. Methods to decrease water solubility include: using a water insoluble salt, complex, or insoluble prodrug; preincorporating the drug into hydrophobic microparticles that can be used as drug particles; or preparing an aqueous medium that the drug is less soluble in, for example, by adjustment of pH or ionic strength, or by adding salts or additives. If the substance to be delivered is rendered less water soluble by adjustment of pH or ionic strength, the resulting liposheres can be isolated by filtration or centrifugation and reconstituted with an appropriate buffer solution prior to use.

Bioactive peptides and proteins can be preincorporated into microparticles of a hydrophobic solid phase, such as tristearin (melting point 65° C.), that can then be incorporated into liposheres with a vehicle having a lower melting point, such as ethyl stearate (melting point 35° C.), to avoid melting the tristearin particles containing the protein. In this form, the tristearin-protein particles are the hydrophobic "drug" which is dispersed in the ethyl stearate liposphere. The formulations can then be freeze dried and reconstituted prior to use.

II. Selection of the Phospholipid Coating

The solid core of the liposphere is coated with one or more phospholipids that are embedded into the surface of the solid core during manufacture. Mixtures of two or more phospholipids can be used to vary the surface properties and reactivity of the liposphere.

A phospholipid is a phosphorylated diacylglyceride molecule or its derivative. The parent structure is diacylglycerol phosphate, or phosphatidic acid. Phosphatidyl choline (lecithin) is the choline ester of phosphorylated diacylglyceride. Synthetic lethicin is available with acyl chain lengths ranging from 4 to 19 carbons. The preferred lecithins for biological applications are those with alkyl chain lengths in the biological range (10–18 carbons). Naturally occurring lethicin can be obtained from a variety of sources such as egg or bovine heart. Unsaturated lecithins (dioleoyl; dilinoleoyl; alpha-palmitoyl, beta oleoyl; alpha palmitoyl, beta linoleoyl; and alpha oleoyl, beta palmitoyl) are also available. Dianachidonyl lecithin (highly unsaturated and a prostaglandin precursor) is also available, as is alpha palmito beta myristoyl lethicin.

A molecule somewhat structurally related to phosphatidic acid, sphingomyelin, is also suitable for use in the coating of lipospheres.

Certain phospholipids, such as phosphatidic acid, phosphatidyl serine, phosphatidyl inositol, cardiolipin (diphosphatidyl glycerol), and phosphatidyl glycerol, react with calcium in serum causing liposphere aggregation or the binding of lipospheres to cell membranes. These unfavorable reactions can be minimized by using in lipospheres for biological applications these phospholipids only in combination with non-calcium binding phospholipids such as phosphotidylcholine. Phosphatidic acid is available from egg or can be prepared synthetically (dimyristoyl, dipalmitoyl and distearoyl derivatives are available from Calbiochem). Bovine phosphatidyl serine is also available commercially (Sigma Chemical Co., St. Louis, Mo.). Phosphatidyl inositol is available from plant or bovine sources. Cardiolipin is available from bovine or bacterial sources. Phosphatidyl glycerol is available from bacterial sources and is prepared synthetically.

Phosphatidylethanolamine in the pure state self-aggregates in a calcium-independent fashion, and is believed to have strong tendencies to aggregate with cell membranes. In lipospheres for biological applications, it should be used only in combination with non-aggregating phospholipids. Phosphatidyl ethanolamine is available as isolated from egg, bacteria, bovine, or plasmalogen or as the synthetic dioctadecanoyl, dioleoyl, dihexadecyl, dilauryl, dimyristoyl and dipalmitoyl derivatives.

Steroids such as cholesterol (a natural constituent of membranes), estrogens (such as estriol, estrone, estradiol and diethylstilbestrol), and androgens (such as androstenedione and testosterone) cannot function alone as the liposphere coating but can be incorporated into a phospholipid membrane to increase the membrane's stability and decrease its reactivity.

Amphiphiles can be added to the phospholipid coating to alter the surface charge on the liposphere. Examples of amphiphiles that provide a positive charge to the coating are protonated long chain alkyl amines such as stearylamine or the corresponding secondary, tertiary or quaternary substituted amines. Examples of amphiphiles that provide a negative charge are arachidonic acid and other fatty acids.

Membrane-active agents such as nystatin, amphotericin B and gramicidin have been shown to bind to the surfaces of phospholipid membranes and change their permeability. They will also alter the reactivity of the lipospheric coating.

III. Method of Preparation of Lipospheres

Lipospheres are prepared by: (1) melting the substance to be delivered, or dissolving or dispersing the substance to delivered in a molten vehicle to form a liquid of the substance to be delivered which can be solidified without changing vehicles; (2) adding phospholipid along with an aqueous medium to the melted substance or vehicle at a temperature higher than the melting temperature of the substance or vehicle; (3) mixing the suspension at a temperature above the melting temperature of the vehicle, until a homogeneous fine preparation is obtained; and then (4) rapidly cooling the preparation to room temperature or below.

Suitable methods of mixing the suspension include mechanical shaking, mechanical stirring, fine mixing using homogenizers, and sonication techniques.

The particle size, particle distribution, and lipid coating can be altered by varying the concentration and properties of the solid vehicle, the lipid, and the mixing method. For intravenous injections, particles should be less than 5 microns in diameter. For subdermal or intramuscular injections, the particle should preferably be less than 250 $\mu$in diameter. Larger particle sizes can be used for oral formulations. Submicron particles are needed for targeted drug delivery.

The product is a uniform fine dispersion of microparticles coated with a layer of a phospholipid, with the hydrophobic side of the phospholipid embedded in the outermost layer of the solid hydrophobic vehicle and the hydrophilic side at the aqueous interface.

The method of preparation of lipospheres described herein is simple and is characterized by high yields, reproducibility, and versatility. The method is further illustrated in the following working examples.

EXAMPLE 1.

Method of Preparation of Lidocaine Liposphere with Tristearin Carrier

To a 20 ml vial was added lidocaine (100 mg), tristearin (500 mg), and L-$\alpha$-lecithin (200 mg). The vial was heated to 65° C. to melt the tristearin and dissolve the lidocaine. Hot buffer solution (60°-70° C., 10 ml; final concentration of lidocaine: 10 mg/ml) was added and the formulation was mixed well by vigorous hand shaking and by vortex for about 5 minutes. The uniform milky like formulation (pH 8.3) was immediately cooled to room temperature by immersing the vial in a dry ice-acetone bath with continued shaking. The pH was adjusted to 7.4 with a 1N HCl solution.

The drug concentration in the inner core of the resulting lipospheres was 9.5 mg/ml (95% yield), as determined by UV absorption (at 240 and 260 nm) of a 100 microliter of the formulation dissolved in 2 ml of a ethanol:dichloromethane mixture.

The particle size was determined in three ways. Particle sizes of less than 10 micron were determined using a Coulter Particle Analyzer. Particle size of greater than 10 microns were determined by passing the formulation through a set of sieves in the range of 200 and 38 microns and weighing the particles remaining on each screen after drying. The shape and size was verified by examining the samples under a microscope.

The particles were spherical in shape with an average particle size of approximately 40 microns. The distribution of the particle sizes is set out in Table 1.

TABLE 1

| Liposphere Particle Size. | |
|---|---|
| Particle size (microns) | Weight % |
| >200 | <1 |
| 106–200 | 12 |
| 68–106 | 8 |
| 38–68 | 5 |
| 1–38 | 67 |
| <1 | 7 |

Similar results were obtained when 1 gram of tristearin or 0.4 gram of L-$\alpha$-lecithin was used.

EXAMPLE 2.

Method of Preparation of Tristearin Liposphere

The preparation method was identical to that of example 1 but without lidocaine. The particle size and shape of the resulting liposheres were similar to that of the liposheres of Example 1.

EXAMPLE 3

Method of Preparation of Lidocaine Liposphere With Ethyl Stearate Carrier

To a 20 ml vial was added lidocaine (100 mg), ethyl stearate (500 mg, melting point 34°-35° C.), and L-α-lecithin (200 mg). The vial was heated to 40° C. to melt the ethyl stearate and dissolve the lidocaine. Warm buffer solution (35°-40° C., 10 ml; final concentration of lidocaine 10 mg/ml) was added and the formulation was mixed well by vigorous hand shaking and by vortexing for about 5 minutes. The uniform milky-appearing formulation (pH 8.3) was immediately cooled to a temperature below 20° C. by immersing the vial in a dry ice-acetone bath with continued shaking. The pH was adjusted to 7.4 with a 1N HCl solution.

The resulting liposheres had a drug concentration of 9.8 mg/ml (98% yield). The average particle size was less than 10 microns.

EXAMPLE 4.

Method of Preparation of Lidocaine Liposphere Without Vehicle

To a 20 ml vial was added lidocaine (200 mg) and L-α-lecithin (100 mg from egg yolk). The vial was heated to 70° C. to melt the lidocaine and then hot buffer solution (60°-70° C., 10 ml) was added. The formulation was mixed well by vigorous hand shaking and by vortexing for about 5 minutes. The uniform milky-appearing formulation (pH 8.I) was immediately cooled to room temperature by immersing the vial in a dry ice-acetone bath with continued shaking. The pH was adjusted to 7.4 with a 1N HCl solution.

The resulting liposheres had a drug concentration of 20 mg/ml (100% yield). The particle size ranged from 0.35±0.176 microns.

EXAMPLE 5.

Method of Preparation of Indomethacin Liposphere with Tristearin Carrier

To a 20 ml vial was added indomethacin (100 mg), tristearin (500 mg), and L-α-lecithin (200 mg). The vial was heated to 65° C. to melt the tristearin. The insoluble indomethacin was dispersed uniformly in the melt using a vortex. Hot buffer solution (60°-70° C., 10 ml; final concentration of indomethacin 10 mg/ml) was added and the formulation was mixed well by vigorous hand shaking and by vortex for about 5 minutes. The uniform, milky-appearing formulation (pH 7.1) was immediately cooled to room temperature by immersing the vial in a dry ice-acetone bath with continued shaking. The pH was adjusted to 7.4 with 1N NaOH solution.

The resulting liposheres had a drug concentration of 9.6 mg/ml (96% yield, concentration added: 10 mg/ml) as determined by UV absorption at 308 and 350 nm of 100 microliters of the formulation dissolved in 2 ml of ethanol:dichloromethane mixture. The particles were spherical in shape with an average particle size of 35±30 microns.

EXAMPLE 6.

Method of Preparation of Indomethacin Liposheres with Ethyl Stearate Carrier The preparation and analytical methods were the same as in Example 5 but ethyl stearate, formulated at 40° C. was used instead of tristearin.

The resulting liposheres had a drug concentration of 9.8 mg/ml (98% yield) and the average particle size was 20±12 microns.

EXAMPLE 7

Method of Preparation of Ibuprofen Liposphere without Carrier

The preparation and analytical methods were the same as in Example 4 but ibuprofen (300 mg), formulated at 70° C. was used instead of lidocaine.

The resulting liposheres had a drug concentration of 30 mg/ml, and the particle size was 0.173±0.048 (50%) and 0.49±0.076 (50%) microns.

EXAMPLE 8

Method of Preparation of Ibuprofen Liposphere with Tristearin Carrier

The preparation and analytical methods were the same as in Example 1 but ibuprofen (300 mg) was used instead of lidocaine, formulated at 70° C.

The resulting liposheres had a drug concentration of 30 mg/ml and the particle size was 30±32 microns.

EXAMPLE 9

Method of Preparation of Methotrexate Liposheres with Tristearin Carrier

The preparation and analytical methods were the same as in Example 5 but methotrexate (100 mg) was used instead of indomethacin.

The resulting liposheres had a drug concentration of 9.5 mg/ml and a particle size of 20±10 microns.

EXAMPLE 10

Method of Preparation of Lidocaine Liposheres with Polycaprolactone Carrier

The preparation and analytical methods were the same as in Example 1 but polycaprolactone (500 mg, molecular weight 2000) was used instead of tristearin.

The resulting liposheres had a drug concentration of 9.5 mg/ml and a particle size of less than 10 microns.

EXAMPLE 11

Stability of Liposheres Prepared in Examples 1-9

The concentration, particle size and distribution of the liposhere formulations prepared in Examples 1-9 were evaluated and then the formulations were stored at 25° C. and at 5° C. with the exception of the liposheres of example 4, after one day a supernatant layer was formed over the liposheres that could be reconstituted to a uniform milky-appearing formulation by light shaking for a few seconds. After thirty days, less than 3% of the original drug concentration had been lost. The particle size and distribution were similar to the original formulations.

EXAMPLE 12

Reconstitution of Liposphere Formulations Prepared in Examples 1-9

The formulations prepared in Examples 1-9 (3 ml) were lyophilized to dryness to form a sticky fluffy cake. The cake weight varied according to the amount of solids added. Reconstitution of the cakes by addition of sterile water (3 ml) followed by vortexing for 1 minute resulted in formulations with drug concentration and particle size similar to the original formulation.

EXAMPLE 14

Method of Preparation of Tetracycline Liposomes with Tristearin/Ethyl Stearate Carrier Tetracycline (150 mg) was suspended in a 1 ml dichloromethane solution containing 450 mg tristearin, and then cast on a Petri dish. After solvent evaporation, the resulting film was ground and sieved to a particle size of less than 38 microns. The particles (400 mg) were suspended in 300 mg of molten ethyl stearate containing L-α-lecithin (200 mg) at 40° C. A warm phosphate buffer solution at pH 7.4 (10 ml, 40° C.) was added and the formulation was mixed well by vigorous hand shaking and by vortexing for about 5 minutes. The uniform, milky-appearing formulation (pH 8.3) was immediately cooled to room temperature by immersing the vial in dry ice-acetone bath with continued shaking. The pH was adjusted to 7.4 with a 1N HCl solution.

The resulting liposheres had a drug content of 9 mg/ml and a particle size ranging from 50±40 microns.

EXAMPLE 14

Release Rates from Liposphere Formulations

In vitro experiments to evaluate the release of the drug formulations prepared as in Examples 1, 3, 4, 5, and 6 were carried out using the following procedure.

To standard cellulose dialysis tubing was added 2 ml of the formulation and sealed. The sealed tubes were immersed in 50 ml of phosphate buffer solution pH 7.40 and placed in a 37° C. incubator. The amount of drug released after discrete times was determined by UV absorbance at 240 and 260 nm for lidocaine and 308 and 350 nm for indomethacin. The solution was then replaced with fresh buffer solution. The drug content of the formulations before and after release was determined by UV absorption of a solution of 100 microliters of the formulation in 3 ml dichloromethane:ethanol 2:1 v/v mixture. The results are summarized in Table 2.

As seen in Table 2, drug release is characterized by an initial burst of about 50% of the drug content. About 80% of the lidocaine was released within 24 hours. The remaining 20% was not released from the formulation. Indomethacin was released for over 5 days, to a total of 80% of the original concentration. The remaining 20% was not released from the formulation.

TABLE 2

In vitro Drug Release From Liposphere Formulations

| Time (hours) | Drug Released (%) | | | | |
|---|---|---|---|---|---|
| | Indomethacin | | Lidocaine | | |
| | Ex 5 | Ex 6 | Ex 1 | Ex 3 | Ex 4 |
| 1 | 21 | 22 | 26 | 32 | 37 |
| 5 | 45 | 42 | 48.7 | 57.8 | 59.7 |
| 10 | 60 | 58 | 56.7 | 66.4 | 66.9 |
| 24 | 65 | 66 | 78 | 80 | 82 |
| 48 | 69 | 70 | 79 | 80 | 82 |

TABLE 2-continued

In vitro Drug Release From Liposphere Formulations

| Time (hours) | Drug Released (%) | | | | |
|---|---|---|---|---|---|
| | Indomethacin | | Lidocaine | | |
| | Ex 5 | Ex 6 | Ex 1 | Ex 3 | Ex 4 |
| 72 | 73 | 73 | | | |
| 120 | 82 | 80 | | | |

EXAMPLE 15

Anesthetic Activity of Lidocaine Formulations

Lidocaine formulations were examined for their local anesthetic activity using a Rat Paw Hyperalgesia model, in which a rat is injected with the formulation in the paw. The tolerance to pain caused by increasing weight on the paw was measured with a Randall-Sellito apparatus. The results are expressed as the weight tolerated by the animal divided by 10 (the higher the number, the more tolerant the animal is to pain and therefore the more effective the release of drug from the liposphere).

The experimental protocol is as follows. Animals (six 250-300 gram rats in each group) received drug (200 microliter, subplantar) at time 0 in both hind feet. One hour prior to measurement carrageenan (which includes inflammation and makes the animal's paw more sensitive to pain) was injected subplantar. Pressure to withdrawal was measured with the Randall-Sellito apparatus. One animal was measured at 6 and 24 hours, another at 8 and 72 hours. The results are summarized in Table 3.

The formulations of Examples 3 and 4 were very effective for more than 24 hours. The formulation of Example 1 was very effective for at least 6 hours with some activity after 24 hours. The standard lidocaine solution was effective for about 2 hours.

TABLE 3

Release of Lidocaine as Measured in the Rat Paw.

| | Pressure | | | |
|---|---|---|---|---|
| Formulation | 6 Hours | 24 Hours | 48 Hours | 72 Hours |
| Controls: | | | | |
| Untreated | 9.15 ± 0.52[a] | 8.76 ± 0.42[a] | 9.04 ± 0.42[a] | 8.89 ± 0.52[a] |
| Carrageenan | 4.14 ± 0.54 | 4.72 ± 0.48 | 4.50 ± 0.36 | 4.64 ± 0.48 |
| Liposheres of Example 2: no drug | 4.27 ± 0.69 | 4.85 ± 0.58 | 4.46 ± 0.50 | 4.56 ± 0.53 |
| +200 μl of 2% Lidocaine: | 6.42 ± 1.51[b] | 3.82 ± 0.56[b] | N.T. | N.T. |
| Liposheres of Example 3: | 9.65 ± 1.71 | 7.11 ± 0.65 | 5.46 ± 0.67 | N.A. |
| Liposheres of Example 4: | 9.52 ± 1.75[c] | 6.97 ± 0.69[d] | 5.54 ± 0.82 | 4.75 ± 1.03 |
| Liposheres of Example 1: | 9.45 ± 1.72[e] | 5.78 ± 0.78 | 5.10 ± 0.62 | 4.36 ± 0.75 |

N.T. = Not Tested
n = 6 in each group.
[a]Result is a group mean of all 24 "unknown preparation" animals and are listed simply to note "normal" tolerance.
[b]Not different from carrageenan alone (p > 0.05).
[c]p = 0.19 compared to control Example 2.
[d]p = 0.0407 compared to control Example 2.
[e]p = p.021 compared to control Example 2.

EXAMPLE 6

Antiinflammatory Effect of Indomethacin and Ibuprofen Lipospheres

Liposheres containing indomethacin and ibuprofen were evaluated for their anti-inflammatory effect using a Nsaid Rat Paw Edema model. The results are provided in Table 4.

Animals (6 in each group) received drug intraperitoneally at t=0. Carrageenan was administered subplantar two hours prior to edema measurement. Each animal could be used for two measurements, one in each foot. Edema was measured with a plethysmometer.

Both indomethacin liposphere formulations were active for more than three days, while the reference indomethacin solution was active for less than 6 hours. The ibuprofen liposphere formulations were active for at least 24 hours.

TABLE 4

Effectiveness of Liposphere Preparations in Treatment of Rat Paw Edema.

| Formulation | Edema, ml | | | |
| --- | --- | --- | --- | --- |
| | 6 Hours | 24 Hours | 48 Hours | 72 Hours |
| control: Carrageenan | 1.11 ± 0.05 | 1.05 ± 0.06 | 1.06 ± 0.08 | 1.14 ± 0.11 |
| Liposheres of Example 2: no drug, 1 ml | 1.04 ± 0.06 | 1.08 ± 0.12 | 1.02 ± 0.04 | 1.05 ± 0.07 |
| +2 mg/kg Indomethacin i.p. | 0.94 ± 0.12[b] | 0.98 ± 0.06[a] | 1.06 ± 0.11 | 1.04 ± 0.06 |
| Lispospheres of Example 5: | 0.37 ± 0.09 | 0.04 ± 0.04 | 0.26 ± 0.06 | 0.51 ± 0.03 |
| Liposheres of Example 6: | 0.29 ± 0.07 | 0.05 ± 0.06 | 0.19 ± 0.04 | 0.44 ± 0.06 |
| Liposheres of Example 8: | 0.18 ± 0.06 | 0.11 ± 0.04 | N.T. | N.T. |
| Liposheres of Example 7: | 0.15 ± 0.09 | 0.39 ± 0.25 | N.T. | N.T. | n = 6 in each except ibuprofen n = 2 for Example 8 and n = 4 for Example 7.
[a]Test animals suffered acute intestinal failure ("paralytic ileus").
[b]Not different from carrageenan alone.

EXAMPLE 17

Dexamethasone and Triamcinolone Liposphere Formulations

Dexamethasone and triamcinolone are relatively water soluble steroids. These drugs were formulated as follows: dexamethasone or triamcinolone powder (100 mg, particle size less than 20 $\mu$) was dispersed in 300 mg molten tristearin and cooled to room temperature. The solid was ground and sieved to particle size of less than 100 $\mu$. The particles (200 mg) were suspended in 200 mg of molten ethyl stearate containing L-α-lecithin (100 mg) at 40° C. Warm phosphate buffer solution, pH 7.4 (5 ml, 40° C.) was added and the formulation mixed well by vigorous shaking and by vortexing for about five minutes. The uniform, milky-appearing formulation was immediately cooled to room temperature by immersing the vial in a dry ice-acetone bath with continuous shaking. The preparation was freeze dried for 24 hours and the fluffy, sticky powder was reconstituted before injection. The drug content was 4.7 mg/ml and the particle size was less than 250 microns.

The formulations were both tested for their biological activity using the same experimental model and methods as in example 16. The control consisted of 10 mg drug/ml phosphate buffer. The formulations were active for at least three days, in contrast to the reference solutions which exhibited activity for approximately 24 hours.

Modifications and variations of the present invention, a method and compositions for preparing liposheres for controlled delivery of substances, will be obvious to those skilled in the art from the foregoing detailed description. Such modifications and variations are intended to come within the scope of the appended claims.

I claim:

1. A liposphere comprising
   a core formed of a hydrophobic material existing as a solid at a temperature of at least 30° C., and
   a phospholipid coating surrounding the core, wherein the hydrophobic ends of the phospholipid are embedded in the solid core and the hydrophilic ends of the phospholipid are exposed on the surface of the liposphere,
   the combination forming a spherical structure having an average particle diameter of between 0.3 and 250 microns.

2. The liposphere of claim 1 further comprising an active compound within the liposphere.

3. The liposphere of claim 2 wherein the solid core consists of the active compound.

4. The liposphere of claim 2 wherein the solid core includes the active compound and a vehicle for the active compound which in combination with the active compound exists as a solid at 30° C.

5. The liposphere of claim 1 wherein the solid core has a melting point between 30° C. and 120° C.

6. The liposphere of claim 4 wherein the vehicle is selected from the group consisting of natural, regenerated and synthetic waxes, fatty acid esters, high molecular weight fatty alcohols, solid hydrogenated vegetable oils, solid triglycerides, and biodegradable polymers.

7. The liposphere of claim 2 wherein the active compound is selected from the group consisting of nonsteroidal antiinflammatories, local anesthetics, water insoluble anticancer drugs and steroids.

8. The liposphere of claim 2 that is suitable for injection into a patent.

9. The liposphere of claim 2 wherein the active compound is selected form the group consisting of food additives, pesticides, herbicides, insecticides, pheromones, colors and inks.

10. A method of preparation of a liposphere comprising:
   (a) providing a hydrophobic liquid which forms a solid at a temperature of at least 30° C.;
   (b) adding to the liquid hydrophobic material a phospholipid followed by an aqueous solution at a temperature higher than the melting temperature of the hydrophobic material to form a dispersion;
   (c) mixing the dispersion at a temperature above the melting temperature of the hydrophobic material until a homogeneous fine preparation is obtained; and
   (d) rapidly cooling the preparation to a temperature at which the hydrophobic material solidifies,
   to form a liposphere comprising
   a core formed of a hydrophobic material existing as a solid at a temperature of 30° C., and
   a phospholipid coating surrounding the core, wherein the hydrophobic ends of the phospholipid are embedded in the solid core and the hydrophilic ends of the phospholipid are exposed on the surface of the liposphere, the combination forming a spherical structure having an average particle diameter of between 0.3 and 250 microns.

11. The method of claim 10 further comprising selecting a hydrophobic material that has a melting point between 30° C. and 120° C.

12. The method of claim 10 further comprising providing an active compound to be incorporated within the liposphere.

13. The method of claim 12 wherein the active compound is the hydrophobic material.

14. The method of claim 12 wherein the active compound is dispersed or dissolved in an inert hydrophobic material which in combination with the active compound exists as a solid at a temperature of 30° C.

15. The method of claim 12 further comprising decreasing the water solubility of the active compound before addition to the phospholipid-aqueous solution.

16. The method of claim 12 further comprising preincorporating the active compound into a hydrophobic microparticle before addition of the active compound to the hydrophobic material forming the core of the liposphere.

17. The method of claim 12 further comprising selecting an aqueous solution that the active compound has low solubility in.

18. The method of claim 12 wherein the active compound is a peptide or protein.

19. The method of claim 14 wherein the hydrophobic material is selected from the group consisting of natural, regenerated and synthetic waxes, fatty acid esters, high molecular weight fatty alcohols, solid hydrogenated vegetable oils, solid triglycerides, and biodegradable polymers.

20. The method of claim 12 further comprising selecting the active compound to be delivered from the group consisting of nonsteroidal antiinflammatories, local anesthetics, water insoluble anticancer drugs and steroids.

21. The method of claim 12 further comprising selecting the active compound to be delivered from the group consisting of food additives, pesticides, herbicides, insecticides, pheromones, colors and inks.

* * * * *